United States Patent
Gazvani et al.

(10) Patent No.: US 11,510,867 B2
(45) Date of Patent: Nov. 29, 2022

(54) IMPLANTABLE MEDICAMENT DELIVERY SYSTEM

(71) Applicant: Reproductive Medicine and Gynaecology Associates Limited, Stockport (GB)

(72) Inventors: Mehmet Rafet Gazvani, Stockport (GB); Halil Ibrahim Tekin, Stockport (GB)

(73) Assignee: REPRODUCTIVE MEDICINE AND GYNAECOLOGY ASSOCs. LTD, Stockport (GB)

( * ) Notice: Subject to any disclaimer, the term of this patent is extended or adjusted under 35 U.S.C. 154(b) by 713 days.

(21) Appl. No.: 16/324,473

(22) PCT Filed: Aug. 21, 2017

(86) PCT No.: PCT/GB2017/052462
§ 371 (c)(1),
(2) Date: Feb. 8, 2019

(87) PCT Pub. No.: WO2018/037214
PCT Pub. Date: Mar. 1, 2018

(65) Prior Publication Data
US 2019/0167575 A1    Jun. 6, 2019

(30) Foreign Application Priority Data

Aug. 23, 2016 (GB) ..................................... 1614367

(51) Int. Cl.
*A61K 9/00* (2006.01)
*A61M 31/00* (2006.01)
(Continued)

(52) U.S. Cl.
CPC .............. *A61K 9/0039* (2013.01); *A61F 6/14* (2013.01); *A61F 6/22* (2013.01); *A61K 9/0024* (2013.01);
(Continued)

(58) Field of Classification Search
CPC ............ A61M 31/002; A61M 37/0069; A61M 31/00; A61M 31/007; A61M 2205/04;
(Continued)

(56) References Cited

U.S. PATENT DOCUMENTS 3,608,549 A    9/1971 Merrill
4,016,251 A    4/1977 Higuchi
(Continued)

FOREIGN PATENT DOCUMENTS

WO    00 28968 A1    5/2000
WO    2004 037318 A2    5/2004

*Primary Examiner* — Kami A Bosworth
*Assistant Examiner* — Alexandra Lalonde
(74) *Attorney, Agent, or Firm* — Craft Chu PLLC; Andrew W. Chu

(57) ABSTRACT

A flexible implantable contraceptive disc device is disclosed which can be inserted inside the female body, such as inside the uterus, is disclosed. The disc device can be bent and inserted into a laparoscopy tube, which allows it to be delivered to an appropriate location inside a female subject. The disc device has three layers, a central core silicon reservoir containing an active ingredient, such as a contraceptive progesterone, which is sandwiched and encased by upper and lower porous silicon casings. The casings are porous to the contraceptive, allowing controlled release over a prolonged period of time. The lower casing has a series of micro-hooks around a circumference, allowing the disc device to be attached to a desired tissue by rotating the disc device such that the hooks engage with the desired tissue. Such a device is easier to insert, and to remove, than a (Continued)

rod-like rigid plastic T-shape IUDs which are considerably larger, also and more expensive to manufacture.

10 Claims, 1 Drawing Sheet

(51) Int. Cl.
    *A61F 6/14*     (2006.01)
    *A61F 6/22*     (2006.01)
    *A61L 31/14*     (2006.01)
    *A61L 31/16*     (2006.01)

(52) U.S. Cl.
    CPC ........... *A61M 31/002* (2013.01); *A61F 6/144* (2013.01); *A61F 2250/0067* (2013.01); *A61L 31/148* (2013.01); *A61L 31/16* (2013.01); *A61L 2300/602* (2013.01); *A61L 2300/608* (2013.01)

(58) Field of Classification Search
    CPC .. A61K 9/0024; A61K 9/0034; A61K 9/7007; A61K 9/0039; A61L 31/16; A61F 6/22; A61F 6/14; A61F 6/142
    See application file for complete search history.

(56) References Cited

U.S. PATENT DOCUMENTS

| | | | |
|---|---|---|---|
| 4,188,951 A | 2/1980 | Higuchi | |
| 2005/0234543 A1* | 10/2005 | Glaser | A61B 17/12022 623/1.42 |
| 2007/0269487 A1* | 11/2007 | de Juan, Jr. | A61F 9/0026 424/427 |
| 2009/0012350 A1* | 1/2009 | Tihon | A61F 2/004 600/30 |
| 2010/0152704 A1* | 6/2010 | Lee | A61L 29/16 604/517 |

* cited by examiner

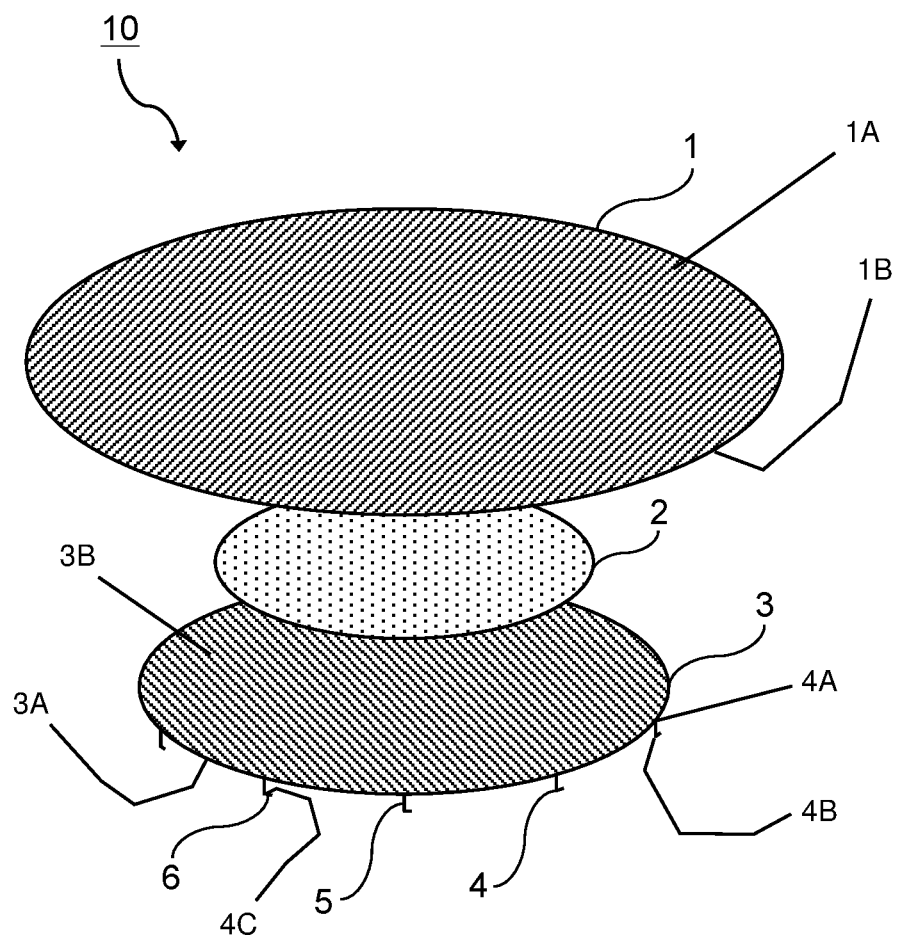

IMPLANTABLE MEDICAMENT DELIVERY SYSTEM

CROSS-REFERENCE TO RELATED APPLICATIONS

See Application Data Sheet.

STATEMENT REGARDING FEDERALLY SPONSORED RESEARCH OR DEVELOPMENT

Not applicable.

THE NAMES OF PARTIES TO A JOINT RESEARCH AGREEMENT

Not applicable.

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not applicable.

STATEMENT REGARDING PRIOR DISCLOSURES BY THE INVENTOR OR A JOINT INVENTOR

Not applicable.

BACKGROUND OF THE INVENTION

1. Field of the Invention

The present application relates to an implant, such as a medical implant, which can be a medicament or drug delivery system. Preferably the implant is an IUD (intra-uterine device or delivery system) or a contraceptive.

2. Description of Related Art Including Information Disclosed Under 37 CFR 1.97 and 37 CFR 1.98

IUDs are well known as contraceptive devices. These generally have a rigid support, and release an active ingredient over time. They are usually T- or V-shaped, held in the uterus by their shape. However, such T-shaped devices are relatively large, and are normally made of a rigid plastic material, making them relatively expensive to make, and they can be difficult to both insert and remove. They can also be uncomfortable and require medical assistance for either insertion, or more usually, to have them removed after several years. The aim of the present invention is to solve or at least mediate one or more of these problems. The invention therefore aims to provide a medicament delivery system, which could be used as an IUD or a contraceptive or a drug delivery system for another tissue, which is relatively small in size and shape, and can be flexible to allow easier insertion into the body. In view of its shape maybe more comfortable (and even unnoticeable) to the patient, and may be cheaper to manufacture.

BRIEF SUMMARY OF THE INVENTION

Thus, according a first aspect of the invention, there is provided an implant, in particular a medical implant or implantable device, or a medicament (or drug) delivery system. This can comprise a (inner) medicament reservoir and a (e.g. outer) porous matrix, which is suitably porous to the medicament, preferably a silicon matrix. The implant can also have tissue attachment means, in order to secure the device to the relevant tissue.

BRIEF DESCRIPTION OF THE SEVERAL VIEWS OF THE DRAWINGS

The present invention will now be described by way of example only, and with reference to the accompanying drawings.

FIG. 1 is a schematic illustration of an embodiment of the present invention.

DETAILED DESCRIPTION OF THE INVENTION

Device

The device of the invention is an implantable one, such as a medical implant. It can be designed to be located or fitted inside the body. It usually contains one or more medicaments (or drugs, the terms are used interchangeably) and can therefore provide a medicament delivery system.

Flexibility

The device is preferably flexible, such as wholly flexible (there are no non-flexible parts). Suitably it will not be rigid, and so it may comprise no rigid parts and/or components. It can be bent, or it can be curved, in other words the device can be deformable. Preferably it can flex or bow in a number of different directions, along several axes or degrees of symmetry. Suitably the device is foldable, or can be curled.

The implant may therefore be relatively supple, pliable or resilient.

This allows the implant to be inserted into the body using a tube, for example a laparoscopy tube. The device may be inserted into the body, preferably via a tube or cylinder, for example one that is between 5 mm and 10 mm in diameter. Preferably therefore the implant of the invention can be insertable into the body via a tube, which may make both insertion, and removal, easier than the traditional T-shape plastic IUD.

Shape

The device can be any regular or irregular shape, but preferably has two planar faces.

Preferably the device is flat, or substantially flat. It may effectively exist in one plane, or maybe generally planar.

Suitably it contains no plastic, or rigid plastic, parts or components.

The device may be substantially square, rectangular or, more preferably, circular.

Preferably the device is substantially circular. The device may therefore resemble a disc or be substantially disc-like. This means the device can easily be curled or folded so that it can be inserted into a (e.g. laparoscopy) tube.

Size

Preferably the dimensions of the device are such that one side is at least 5 mm (e.g. if square or rectangular), with a maximum of 10 mm or 15 mm. If it is substantially circular, then the diameter is preferably more than 5 mm, such as more than 8 mm, or preferably no more than 10 mm or 15 mm.

Preferably the device is able to open up, for example unfurl or uncurl to a generally planar state. This may be the state and shape it was in prior to curling or insertion into a tube. This means that the device can be placed into a tube, and when it exits the tube it can uncurl or unfurl into its original generally flat or planar position or state. The device therefore can in effect have "memory" such that it can return to its original, generally flat or planar state.

Body Locations

Suitably the device can be inserted or implanted into the abdomen, for example the pelvis, pelvic cavity or the pelvic wall. It could be inserted into the uterine body, such as the uterus. However, it can also be inserted into or near the bowel, bladder, peritoneum, fallopian tube, ovary, stomach or intra-peritoneally.

The implant is to be located inside the body, and is therefore capable of internalisation, for example in a body cavity, and is therefore preferably bio-compatible.

Tissue Attachment Means

These means are anchoring means, or body fixing or locating means. It allows the device to be attached or affixed to a desired tissue. The device can therefore be secured to the relevant part of the body. In this way the device can be fastened to a desired tissue or part of the body, in particular located in a cavity.

Preferably such means allow a frictional contact, for example usually a one point of contact. Suitably the implant will lie substantially flat and in contact with the target tissue. If the device is substantially flat, for example generally planar and having two (e.g. opposite) sides, then one side will be suitably in contact with the tissue.

Attachment may be via adhesive, for example a biocompatible glue or other adhesive substance. However, mechanical means of attachment may also be used, for example locating means to attach to the tissue. Preferably one or more (small) micro-hooks can be used in order to attach the device to the desired tissue.

Suitably the device can be located into the tissue by rotation, for example about an axis through the device and perpendicular to it. If the device is a disc, square or rectangle then it can be rotated about an axis passing through (and at right angles) to the approximate centre of the device. Preferably rotation of the device in one direction may allow the device to become attached to the tissue, whereas rotation in another and opposite direction may release the device from the desired tissue.

Suitably there are a plurality of attachment means. If micro-hooks are provided, then preferably these are located around or near the edges of the device.

Medicaments and Drugs

The device could be used to deliver a wide range of medicaments, for example therapeutic substances. It may be a contraceptive. For example, the medicament might be a steroid, for example progesterone, levonorgestrel or desogestrel other steroid or progestogenic compounds include cyproterone acetate, etonogestrel, lynoestrenol, medroxyprogesterone acetate, norethisterone, noresthiothone acetate, norgestimate, drospirenone, gestodene, 19-nor-17-hydroxy progesterone esters, ethinyl testosterone compounds or derivatives thereof, 19-nor-testosterone or derivatives thereof, ethynodiol, dydrogoseterone, norethynodrel, allylestrenol, medrogestone, norgestrienone, ethisterone or dl-norgestrel.

Other medicaments can be omega 3 or omega 6 fatty acids, and angiogenesis inhibitors.

Other therapeutic active substances that can be included can be prostaglandin synthesis inhibitors, such as diclofenac sodium, NSAIDs such as naproxen, indomethacin, ibuprofen, mefenamic acid, flurbiprofen, inhibitors of leukotriene, such as zafirlukast and montelukast, oxytocin antagonists, pancreatic trypsin inhibitors, COX-inhibitors, antifibrinolytic drugs, oestrogens and anti-oestrogens, aromatase inhibitors, cytokine inhibitors, glucocorticoids and progestogens.

Any pharmaceutically acceptable form of any drug or medicament may be employed in the practice of the present invention, e.g., a free base or free acid or a pharmaceutically acceptable salt or ester thereof. Pharmaceutically acceptable salts, for instance, include sulfate, lactate, acetate, stearate, hydrochloride, tartrate, maleate, and the like.

In certain embodiments, drug-containing core of the device comprises from 0.01 mg to 200 mg of the agent. For example, in certain embodiments, the core comprises from 0.01 mg to 100 mg of the drug, such as from 0.05 mg to 20 mg of the agent. In certain embodiments, device comprises a single reservoir which contains from 0.01 to 5 mg of the drug such as from 0.05 to 2 mg, such as from 0.1 to 1 mg of the agent. In certain embodiments, the device comprises more than one reservoir wherein each reservoir contains from 0.5 to 10 mg of the drug.

Preferably the device is a controlled or sustained or gradual release device, allowing for delivery of the medicament over a period of time, for example, at least one, two or six months, up to for example, two, three or five years.

The device may be configured to allow the medicament to be released over time from the reservoir, for example passing through the matrix. The reservoir therefore may contain the drug medicament, therapeutic ingredient, pharmaceutical or drug, as appropriate.

In addition to a therapeutic agent, the drug reservoir may include additional components such as pharmaceutically acceptable carriers or an additional therapeutic agent. In certain embodiments, the reservoir comprises a therapeutic agent and a biocompatible polymer, such as polyvinyl alcohol (PVA), forming a drug core. Biocompatible polymers are known in the art and exemplary polymers are presented herein. Such a drug core may serve to rigidify a drug solution, thus setting an otherwise liquid drug as a solid or semi-solid within the reservoir. The drug core may also serve to delay release of the therapeutic agent from the device. Pharmaceutically acceptable carriers may be added to the drug or medicament for a variety of reasons such as ease of manufacturing, stabilizing the drug or medicament, and altering the viscosity for loading into the device. The drug core may comprise the drug or medicament, a polymer and one or more carriers. The drug core may comprise one or more drug or medicament. The drug core may comprise one or more polymeric agents such a cross-linked polymers or cross-linked gelatins.

The term pharmaceutically acceptable carrier is well known in the art and refers to a pharmaceutically-acceptable material, composition or vehicle, such as a liquid or solid filler, diluent, excipient, solvent or encapsulating material, involved in carrying or transporting any subject composition or component thereof. Each carrier must be "acceptable" in the sense of being compatible with the subject composition and its components and not injurious to the patient. Some examples of materials which may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

Layers

The device may be a single layer, or multi-layer device, for example with two or three or more layers. The medicament may be located in one layer, if only one layer is provided, and may be dispersed or distributed evenly throughout the matrix or single layer, or maybe concentrated in a particular place, for example a reservoir. The medicament may be contained within a single reservoir, or contained within multiple reservoirs in the medicament-containing layer.

Each of the one or more layers has a certain thickness. The thickness of each of the one or more layers may be the same or different. Different combinations of layers and the use of layers of different thicknesses and/or made of different materials may be used to control the release rate of the medicament or drug.

The one or more layers may be made of the same material. Alternatively, the one or more layers may be made of different materials. For example, in a three-layer device, the first and second layer may be made of the same material and the third layer may be made of a different material; the first and third layer may be made of the same material and the second layer made of different material; the second and third layer may be made of the same material and the first layer made of a different material; or the first, second and third layers may all be made of different materials.

In principle the one or more layers may be made of any material, either biodegradable or non-biodegradable, provided said material is biocompatible. The material may be a polymer. As known in the art, the release kinetics of a medicament or drug from a delivery system depends on the molecular weight, solubility, diffusivity and charge of the medicament or drug as well as on the characteristics of the material of the one or more layers, on the percentage of the loading of the medicament or drug, on the distance the medicament or drug must diffuse through the device body to reach its surface and on the characteristics of any material used to make the one or more layers of the device.

The one or more layers may also comprise additional material to further adjust the release rate of one or several of the drug or medicament, for example complex forming agents such as cyclodextrin derivatives to adjust the initial burst of the substance to the accepted or desired level. Auxiliary substances, for example such as tensides, anti-foaming agents, solubilisers or absorption retarders, or a mixture of any two or more of such substances, can also be added in order to impart the desired physical properties to the body of the delivery system.

If the device has two layers, then one layer may comprise the matrix, such as silicon matrix, and there may be a second layer, for example forming the medicament reservoir, and this may be inside or incorporated within the other matrix layer. Preferably the reservoir is wholly contained in, or surrounded by, the matrix. This means that the active substance is suitably encompassed by the matrix. Preferably the matrix is porous, or porosified, so that it is porous to the medicament. The matrix is preferably one that allows the passage of the medicament therethrough. The matrix will generally be bio-compatible.

The matrix is preferably porous silicon, such as biodegradable silicon and may be macro-porous, meso-porous or micro-porous. It can have a pore diameter larger than 50 nm, for example a pore diameter between 20 nm and 50 nm.

If the device has three layers, then preferably the first and third layer, such as the upper and bottom layer, may be silicon layers, preferably porous silicon layers. Suitably these will be inert, bio-compatible, and made of a substance that doesn't itself adhere or fix to the tissue. Preferably there is an upper and lower silicon casing, suitably one of which is porous to the medicament.

The third layer or reservoir maybe a silicon reservoir, for example a core which is not porous. In the case of three layers, the middle reservoir layer can be exposed at the sides, or it may be wholly enclosed by the other two layers and thus surrounded by a porous matrix.

In certain embodiments, a drug-permeable seal or drug-permeable membrane may be used used so as to allow the controlled release of the drug. In certain embodiments, the drug-permeable membrane is a seal that covers one or more openings of the porous silicon body and, in addition, covers surface area beyond the opening. For example, the membrane may cover an entire side or two sides of the device, extending beyond the opening of the reservoir. The membrane may cover multiple openings such as 2, 3 or 4 openings. The reservoir may cover a percentage of the surface area of the particle including the surface of the openings such as at least about 10% of the surface, at least about 20% of the surface, at least about 30%, of the surface, at least about 40% of the surface, at least about 50% of the surface, at least about 60% of the surface or even at least about 70% of the surface, such as from 10-90% of the surface or 10-70% of the surface. In such embodiments, the membrane, similar to the seal, serves to control the release of the drug from the device. The preferred composition of the drug-permeable seal or membrane will vary depending on such factors as the drug, the desired rate of release, and the mode of administration. The identity of the drug may also be a factor in the rate of release, since the size of the molecule, its solubility, and its polarity may play a role in determining the rate of release of the drug. In certain embodiments, the drug-permeable seal or membrane is impermeable to components in a biological environment such as proteins, nucleic acids, carbohydrates, lipids, cells or cellular components.

Exemplary permeable materials suitable for use as seals or membranes are described in U.S. Pat. No. 4,014,335. These materials include, but are not limited to: cross-linked polyvinyl alcohol, polyolefins or polyvinyl chlorides or cross-linked gelatins; regenerated, insoluble, non-erodible cellulose, acylated cellulose, esterified celluloses, cellulose acetate propionate, cellulose acetate butyrate, cellulose acetate phthalate, cellulose acetate diethyl-aminoacetate; polyurethanes, polycarbonates, and microporous polymers formed by co-precipitation of a polycation and a polyanion modified insoluble collagen.

Polysiloxanes

Polysiloxanes, in particular poly(dimethyl siloxane) (PDMS), are suitable for use as the material for the one or more layers as they regulate the permeation rate of medicaments and drugs. Polysiloxanes are physiologically inert, and a wide group of medicaments and drugs are capable of penetrating polysiloxane membranes, which also have the required strength properties. The permeation rate of the medicaments and drugs can be adjusted at a desired level by modifying the polymeric material in a suitable way, e.g. by adjusting hydrophilic or hydrophobic properties of the material using techniques known in the art.

Further examples of suitable materials include, but are not limited to, copolymers of dimethylsiloxanes and methylvinylsiloxanes, ethylene/vinyl acetate copolymers (EVA), polyethylene, polypropylene, ethylene/propylene copolymers, acrylic acid polymers, ethylene/ethyl acrylate copolymers, polytetrafluoroethylene (PTFE), polyurethanes, thermoplastic polyurethanes and polyurethane elastomers, polybutadiene, polyisoprene, poly(methacrylate), polymethyl methacrylate, styrene-butadiene-styrene block copolymers, poly(hydroxyethyl-methacrylate) (pHEMA), polyvinyl chloride, polyvinyl acetate, polyethers, polyacrylonitriles, polyethylene glycols, polymethylpentene, polybutadiene, polyhydroxy alkanoates, poly(lactic acid), poly(glycolic acid), polyanhydrides, polyorthoesters, hydrophilic polymers such as the hydrophilic hydrogels, cross-linked polyvinyl alcohol, neoprene rubber, butyl rubber, hydroxyl-terminated organopolysiloxanes of the room temperature vulcanizing type which harden to elastomers at room temperature following the addition of cross-linking agents in the presence of curing catalysts, one- or two-component dimethylpolysiloxane compositions cured by hydrosilylation at room temperature or under elevated temperatures, as well as mixtures thereof. It is also clear for an expert in the field that suitable materials may be composed of the copolymers of the above mentioned homopolymers.

The structural integrity of the material may be enhanced by the addition of a particulate material such as silica or diatomaceous earth. The elastomers can also be mixed with other additives to adjust elastomer's hydrophilic or hydrophobic properties while taking into account that all additives need to be biocompatible and harmless to the patient.

The one or more layers may be made of a siloxane based elastomer composition comprising at least one elastomer and optionally a non-crosslinked polymer.

The term "elastomer composition" may stand for one single elastomer, the deformation of which caused by the strain is reversible so that the elastomer's shape recovers to a certain level after the strain. The elastomer composition may also be made up of two or more elastomers blended with each other.

The term "siloxane-based elastomer" shall be understood to cover elastomers made of poly (disubstituted siloxanes) where the substituents mainly are lower alkyl, preferably alkyl groups of 1 to 6 carbon atoms, or phenyl groups, wherein said alkyl or phenyl can be substituted or unsubstituted. A widely used and preferred polymer of this kind is poly(dimethylsiloxane) (PDMS).

The methods for the preparation of suitable polymers are given for example in International patent applications WO 00/00550, WO 00/29464 and WO 99/10412

If the device has two layers, then one layer may comprise the matrix, such as silicon matrix, and there may be a second layer, for example forming the medicament reservoir, and this may be inside or incorporated within the other matrix layer. Preferably the reservoir is wholly contained in, or surrounded by, the matrix. This means that the active substance is suitably encompassed by the matrix. Preferably the matrix is porous, or porosified, so that it is porous to the medicament. The matrix is preferably one that allows the passage of the medicament therethrough. The matrix will generally be bio-compatible.

The matrix is preferably porous silicon, such as biodegradable silicon and may be macro-porous, meso-porous or micro-porous. It can have a pore diameter larger than 50 nm, for example a pore diameter between 20 nm and 50 nm.

If the device has three layers, then preferably the first and third layer, such as the upper and bottom layer, may be silicon layers, preferably porous silicon layers. Suitably these will be inert, bio-compatible, and made of a substance that doesn't itself adhere or fix to the tissue. Preferably there is an upper and lower silicon casing, suitably one of which is porous to the medicament.

The third layer or reservoir maybe a silicon reservoir, for example a core which is not porous. In the case of three layers, the middle reservoir layer can be exposed at the sides, or it may be wholly enclosed by the other two layers and thus surrounded by a porous matrix.

Porous Silicon

The one or more layers, particularly the non-drug/medicament containing layer(s), for example the first and third layers of a three-layer device, maybe made of silicon that is made biodegradable, such as through porosification. Such silicon is referred to herein as porous silicon. Porous silicon is usually biocompatible and can be eroded in, or resorbed into, a patient without significant detrimental effect.

The present invention provides devices comprising biodegradable porous silicon structures and methods of manufacturing such devices using porous silicon. Porous silicon structures, unlike crystalline silicon structures, have been shown to biodegrade in vitro and in vivo producing innocuous by-products, i.e., monomeric silicic acid $(Si(OH)4)$. Silicic acid, which is naturally present in blood plasma at levels of less than 1 mg Si/L from the dietary intake of 20-50 mg/day, is readily removed by the kidneys.

The rate of dissolution in biological media varies based on the pore size in the silicon. Very small pores (e.g. nm-$\mu$m diameter) can be introduced into crystalline silicon with a relatively high degree of uniformity and control using conventional integrated circuit and micromachining processing. Also, the high surface area pores of porous silicon can be coated with specific materials by existing silicon processing technology for the adsorption/desorption of liquids or gasses. In addition, the porous silicon can be fabricated as thin membranes, e.g. 50 $\mu$m thick, which may be bonded to other materials, such as Pyrex or glass.

Macroporous silicon has a pore diameter larger than 50 nm, mesoporous silicon has a pore diameter between 2 and 50 nm, while microporous silicon has a pore diameter less than 2 nm. The pore size of the porous silicon affects the rate of biodegradation of the silicon; accordingly, the pore size may be selected on the basis of the intended lifespan of the device.

The porous silicon layer may have a porosity from 4% to 90%. The layer has a porosity from 20% to 70% such as a porosity from 30% to 60% such as a porosity of about 30% or of about 35% or of about 40% or of about 45% or of about 50% or of about 55% or of about 60%. Porosity, as used herein, is a measure of the void spaces in a material, and is measured as a fraction, between 0 and 1, or as a percentage between 0 and 100%.

Other Materials

In addition to and/or as alternatives to porous silicon and/or polysiloxanes, additional naturally occurring or synthetic materials that are biologically compatible may be used in manufacturing the devices of the invention. For example, biologically compatible materials include, but are not limited to: ethyl vinyl acetate, polyvinyl acetate, cross-linked polyvinyl alcohol, cross-linked polyvinyl butyrate, ethylene ethylacrylate copolymer, polyethyl hexylacrylate, polyvinyl chloride, polyvinyl acetals, plasticized ethylene vinylacetate copolymer, polyvinyl alcohol, polyvinyl acetate, ethylene vinylchloride copolymer, polyvinyl esters, polyvinylbutyrate, polyvinylformal, polyamides, polymethylmethacrylate, polybutylmethacrylate, plasticized polyvinyl chloride, plasticized nylon, plasticized soft nylon, plasticized polyethylene terephthalate, natural rubber, polyisoprene, polyisobutylene, polybutadiene, polyethylene, polytetrafluoroethylene, polyvinylidene chloride, polyacrylonitrile, cross-linked polyvinylpyrrolidone, polytrifluorochloroethylene, chlorinated polyethylene, poly(1,4'-isopropylidene diphenylene carbonate), vinylidene chloride, acrylonitrile copolymer, vinyl chloride-diethyl fumarate copolymer, silicone rubbers, especially the medical grade polydimethylsiloxanes, ethylene-propylene rubber, silicone-carbonate copolymers, vinylidene chloride-vinyl chloride copolymer, vinyl chloride-acrylonitrile copolymer, vinylidene chloride-acrylonitride copolymer, gold, platinum, and (surgical) stainless steel.

The body of the device may be modified with agents that enhance biocompatibility or target the device to a specific location. For example, the surface of the silicon may be coated with a biocompatibility agent, e.g., apatite, to improve biocompatibility. Other exemplary silicon modifications suitable for use with the devices disclosed herein are described in U.S. Pat. No. 6,666,214.

Manufacture

The device may be manufactured using standard techniques known in the art. The one or more layers may be manufactured simultaneously or separately followed by their assembly.

The one or more layers may preferably be manufactured by injection or compression moulding. The drug or medicament containing layer can be manufactured by mixing the drug(s) or medicament(s) within the matrix material for example such as polydimethylsiloxane (PDMS) or the components forming the polymer composition as defined above, processed to the desired shape by moulding, casting, extrusion, or by any other appropriate methods known in the art.

The layer(s) not comprising the drug/medicament, if any, for example the first and third layer, can be applied onto the drug/medicament-containing (second) layer according to known methods such as by using extrusion or injection moulding methods, spraying or dipping. As an alternative, the prefabricated non-drug/medicament containing layer(s) can be expanded mechanically for example with a suitable device or by using for example pressurized gas, such as air, or by swelling it in a suitable solvent, such as cyclohexane, diglyme, isopropanol, or in a mixture of solvents, where after the swollen non-drug/medicament containing layer(s) is mounted onto the drug/medicament containing layer(s). When the solvent evaporates, the non-drug/medicament containing layer(s) tighten on the core.

The one or more layers may be fixed on a frame. Preferably, said frame is not rigid and allows the device to unfurl or uncurl as described above. The one or more layers can be fixed on the frame by using known methods.

The drug/medicament containing layer(s) can also be prepared for example by using a coextrusion method. In such a method a drug/medicament is mixed within the matrix composition, and processed to the desired shape and size by using known extrusion methods. Further layers may then be applied onto the drug/medicament containing layer(s).

To improve the visualization and the detection of the device in vivo, for example in an intrauterine system for example in X-ray or an ultrasound examination, the device may comprise inert metal clips, rings or sleeves, or an inert metal coating on at least part of the device, or metal powder, metal particles or X-ray contrast agents mixed with the raw materials of the device.

Medical Uses

The device can be used to deliver a drug to a target site in the body of a subject. Preferably the subject is a human.

In particular, the device can be used as a contraceptive. It can be used to prevent or suppress abnormal endometrial growth it may be able to prevent ovulation, and thereby reduce endometrial build-up or thickness. It may also be able to reduce menstrual blood loss. The device may have a substance capable of suppressing abnormal or irregular endometrial bleeding or a substance having progestogenic activity, and may reduce and/or eliminate abnormal or excessive bleeding.

Preferably the matrix allows for the release rate for 50 to 100 micrograms per day, for example of a progesterone, or for 20 to 30 micrograms per day for levinolgestrol, or for desogestrel a range of 1 to 5 micrograms per day.

The invention will now be described by way of illustration only, with regard to the following Examples.

FIG. 1 shows one embodiment of the present invention, which is a three-layer drug delivery system. FIG. 1 is an exploded view from above of the drug delivery system in accordance with the present invention. In the embodiment of FIG. 1, the upper layer is a porous silicon upper casing, as is the lowest and third layer. The middle layer is a silicon reservoir containing levonorgestrel (52 mg).

Example 1

A flexible intrauterine contraceptive device (IUD) 10 in the form of a disc, and which is capable of insertion into the uterus by a laparoscopy tube, is manufactured using a three layer drug delivery system. A central core drug reservoir or medicament reservoir 2, containing levonogestrel, is manufactured in a disc-like form, of 5 mm diameter. The silicon reservoir is sandwiched by two porous silicon casings 1, 3 (upper casing 1, lower casing 3). The casings, at their outer edges, contact each other, so that the central silicon reservoir 2 is completely encased by porous silicon (upper casing has an upper outer planar surface 1A and an upper inner planar surface 1B, the lower casing has a lower outer planar surface 3A and a lower inner planar surface 3B) in a flat configuration allowing the contraceptive progesterone to pass therethrough, in a controlled release fashion, usually over about a year. The micro-hooks 4 attach to the lower outer planar surface 3A of the lower casing 3, and the micro-hooks 4 are circumferentially spaced around the edge of the disc. A number of micro-hooks 4 are able to engage the tissue in the uterus. The upper and lower casings 1, 3 are thin, planar, and made of porous silicon and are simply pressed together under pressure to encase the silicon reservoir 2 there within.

In order to insert the device 10 into a human female, the flexible disc, of about 1 cm in diameter, is folded into a laparoscopy tube (folded configuration), which is then inserted through the patient's skin and the uterus wall. It is then located on an inner surface of the uterus. The micro-hooks 4 are arranged such that when rotating the disc clockwise the micro-hooks 4 do not engage with the tissue. However, once the correct location for the device 10 has been decided, the disc device 10 is manipulated anti-clockwise using the laparoscopy instrument (not shown) so that the hooks 4 engage and partially penetrate the surface of the uterus wall, to keep the disc 10 secure and in place. The device 10 can stay attached to the uterus wall for up to two years.

As described, the micro-hooks 4 can be used in order to attach the device 10 to the desired tissue. As shown in FIG. 1, the plurality of micro-hooks 4 are disposed around or near the edges of the device 10. Each of the micro-hooks 4 has a length portion 5 or shank, and a tissue engaging projection 6 or member or bend which allows the device 10 to be releasably attached to the tissue. In a preferred embodiment, the micro-hooks 4 are orientated such that the device 10 can be located in the tissue by rotation in a clockwise direction. In particular, to insert the device 10, the bend or tissue engaging projection 6 of each micro-hook 4 initially abuts against the tissue and rotation clockwise causes the bend or tissue engaging projection 6 to penetrate the surface of the tissue and become embedded therein. In this manner, the device 10 can stay securely attached to the tissue until it is removed by rotation of the device 10 in the opposite direction.

In the embodiment of the invention shown in FIG. 1, the device 10 is rotated clockwise to attach it to the tissue. Equally the skilled person will appreciate that each of micro-hooks 4 could be orientated in a generally opposite configuration, such that the device 10 has to be rotated in an anticlockwise manner to attach it to the tissue, and subsequently rotated clockwise to remove it.

The micro-hooks 4 are each formed from a thin wire, and having an outer diameter which corresponds generally with hypodermic needle gauges 28GA to 34GA. Therefore the outer diameter of the wire forming the micro-hooks 4 is between around 0.18 mm and around 0.36 mm. Although not shown in FIG. 1, the end of each bend or tissue engaging projection 6 includes a bevel 4C that forms a tip that is sharp enough to pierce the tissue.

The length of the shank 5 (having a proximal end 4A and a distal end 4B) which extends outwardly from the lower casing 3 (and as measured from the face of the lower casing 3 to the start of bend or tissue engaging projection 6 of the plurality of micro-hooks 4) is around 0.5 mm to around 1.5 mm. The length of the bend or tissue engaging projection 6 (as measured from the start of the bend 6 projecting from the shank or length portion 5 to the tip of each bend or tissue engaging projection 6 of the plurality of micro-hooks 4) is around 0.25 mm to around 0.75 mm.

The angle formed between the shank or length portion 5 and bend or tissue engaging projection 6 of the plurality of micro-hooks 4 is between around 90° and 135°. This allows the device 10 to be inserted easily into the target site in the body.

The micro-hooks 4 can be formed from biocompatible materials which are pharmacologically inert. The micro-hooks 4 described herein are generally made of a heat-treatable stainless steel or carbon steel.

The device 10 used in this experiment is shown in FIG. 1.

Example 2

A device similar to that made in Example 1, is in FIG. 1 was manufactured. The active ingredient was desogestrel, adapted to be delivered at a rate of 0.1 to 0.7 micrograms per day.

Example 3

A device similar to that in FIG. 1, and as prepared in Example 1, was prepared. However, instead of having three layers, it only had two, and does not contain a silicon reservoir. Instead, the active contraceptive ingredient, progesterone, was instead distributed through the porous silicon casing.

It will be obvious to those skilled in the art that variations of the present invention are possible and it is intended that the present invention may be used other than as specifically described herein.

We claim:

1. An implantable medicament delivery system, comprising:
   a medicament reservoir;
   a porous casing being flexible and being comprised of an upper casing and a lower casing, said medicament reservoir being placed between said upper casing and said lower casing, said upper casing being connected to said lower casing so as to encase said medicament reservoir,
   wherein said upper casing has an upper outer planar surface and an upper inner planar surface, said upper inner planar surface facing said medicament reservoir,
   wherein said lower casing has a lower outer planar surface and a lower inner planar surface, said lower inner planar surface facing said medicament reservoir,
   wherein said porous casing has a flat configuration with said upper outer planar surface, said upper inner planar surface, said lower outer planar surface and said lower inner planar surface being flat,
   wherein said porous casing has a folded configuration with said upper outer planar surface, said upper inner planar surface, said lower outer planar surface and said lower inner planar surface being bent so as to pass through a tube for insertion into an installation site, and
   wherein said porous casing is actuatable between said flat configuration and said folded configuration; and
   a tissue attachment means on said lower outer planar surface of said lower casing, said lower outer planar surface having a lower outer planar surface edge,
   wherein said tissue attachment means is comprised of a plurality of micro-hooks being disposed around said lower outer planar surface edge, each micro-hook of said plurality of micro-hooks having a rotation orientation, and
   wherein said rotation orientation of each micro-hook of said plurality of micro-hooks is aligned in said flat configuration so as to only engage a smooth peritoneal surface by rotation of said porous casing in a single direction and to remain movable along the peritoneal surface until said rotation in said single direction.

2. The system, according to claim 1, wherein said porous casing has a shape selected from a group consisting of: square, rectangular, and disc.

3. The system, according to claim 1, wherein said porous casing is further comprised of an additional layer between said upper layer and said lower layer.

4. The system, according to claim 1, wherein said porous casing is comprised of a silicon matrix.

5. The system, according to claim 1, wherein each micro-hook of said plurality of micro-hooks is comprised of:
   a length portion projecting from the porous casing with a proximal end and a distal end, and
   a tissue engaging projection at said distal end.

6. The system, according to claim 1, wherein each micro-hook of said plurality of micro-hooks has an outer diameter of 0.18 mm to 0.36 mm.

7. The system, according to claim 5, wherein said tissue engaging projection is comprised of a bevel-4G.

8. The system, according to claim 5, wherein said length portion has a length of 0.5 mm to 1.5 mm; and wherein said tissue engaging projection has a length 0.25 mm to 0.75 mm.

9. The system, according to claim 8, wherein said length portion and said tissue engaging projection form an angle between 90 to 135 degrees.

10. The system, according to claim 1, wherein each micro-hook of said plurality of micro-hooks is comprised of at least one of a group consisting of: stainless steel and carbon steel.

* * * * *